United States Patent [19]
Ansmann et al.

[11] Patent Number: 5,863,461
[45] Date of Patent: Jan. 26, 1999

[54] WATER-IN-OIL EMULSIONS

[75] Inventors: Achim Ansmann, Erkrath; Joachim Conradi, Duesseldorf; Rolf Kawa, Monheim; Ludwig Schieferstein, Ratingen, all of Germany

[73] Assignee: Henkel Kommanditgesellschaft auf Aktien, Duesseldorf, Germany

[21] Appl. No.: 849,583

[22] PCT Filed: Nov. 23, 1995

[86] PCT No.: PCT/EP95/04628

§ 371 Date: Jul. 30, 1997

§ 102(e) Date: Jul. 30, 1997

[87] PCT Pub. No.: WO96/16728

PCT Pub. Date: Jun. 6, 1996

[30] Foreign Application Priority Data

Dec. 2, 1994 [DE] Germany .......... 44 42 966.5

[51] Int. Cl.⁶ .............. B01J 13/00; B01F 17/36
[52] U.S. Cl. .......... 252/309; 252/314; 252/356; 424/401; 514/937
[58] Field of Search .............. 252/309, 314, 252/356; 424/401; 514/937

[56] References Cited

U.S. PATENT DOCUMENTS

| | | | |
|---|---|---|---|
| 2,269,529 | 1/1942 | Goldsmith | 252/356 X |
| 3,776,857 | 12/1973 | Lindner | 252/356 X |
| 3,926,840 | 12/1975 | Wendler et al. | 252/309 X |

FOREIGN PATENT DOCUMENTS

| | | |
|---|---|---|
| 0 000 424 | 1/1979 | European Pat. Off. |
| 0 007 731 | 2/1980 | European Pat. Off. |
| 0 033 170 | 8/1981 | European Pat. Off. |
| 0 049 766 | 4/1982 | European Pat. Off. |
| 24 30 342 | 1/1975 | Germany . |
| 42 02 065 | 7/1993 | Germany . |
| 43 15 172 | 11/1994 | Germany . |
| 2 117 398 | 10/1983 | United Kingdom . |
| 93/23450 | 11/1993 | WIPO . |

*Primary Examiner*—Richard D. Lovering
*Attorney, Agent, or Firm*—Ernest G. Szoke; Wayne C. Jaeschke; Glenn E.J. Murphy

[57] ABSTRACT

Water-in-oil emulsions of preferably polar oils are prepared by adding as emulsifiers or stabilizers 0.1 to 10% to weight, relative to the oil phase, of block polyesters of the general formula (I) $R^1CO-(OR^2CO)y-(OC_2H_4)-O-(COR^2O)z-COR^1$, in which $R^1CO$ is an acyl group with 1–22 C-atoms or a hydroxyacyl group derived from a fatty acid with 16–22 C-atoms or a hydroxyacyl group $(OR^2CO)$ derived from a fatty acid with 16–22 C-atoms, x is a number from 5 to 150 and y and z are numbers from 2 to 75, the group $(OC_2H_4)$ x making up 10 to 20% by weight of the total molecular weight.

9 Claims, No Drawings

WATER-IN-OIL EMULSIONS

This application is a national stage filing under 35 U.S.C. § 371 of international application PCT/EP95/04628, filed Nov. 23, 1995.

BACKGROUND OF THE INVENTION

This invention relates to a process for the production of water-in-oil emulsions, more particularly of polar oil components, using block copolyesters of hydroxyfatty acids and polyether glycols as emulsifiers and stabilizers.

DISCUSSION OF THE RELATED ART

The use of block copolyesters of hydroxyfatty acid oligomers and polyethylene glycols as surfactants and emulsifiers is known from various publications. Thus, DE 24 30 342 A1 describes such copolyesters as dispersions aids for hydrocarbon oils. EP 0 000 424 B1 describes block copolymers of 12-hydroxystearic acid oligomers and polyethylene glycols as co-emulsifiers for emulsifying diesel oils.

However, it has been found that the block copolymers described in those documents, which contain 30 to 62% by weight of polyethylene glycol units, are unsuitable for emulsifying water in polar oil components.

In DE 43 15 172 A1, it is proposed to use a combination of the block copolymers known from EP 0 000 424 B1 with other w/o emulsifiers having an HLB value of 3 to 7 for emulsifying water in triglyceride oils.

SUMMARY OF THE INVENTION

It has surprisingly been found that, by reducing the percentage content of the hydrophilic group of such block copolyesters, the water-in-oil emulsifying properties can be improved which has a favorable effect for polar oil components in particular.

Accordingly, the present invention relates to the use of block copolyesters corresponding to general formula I:

$$R^1CO\text{---}(OR^2CO)_y\text{---}(OC_2H_4)_x\text{---}O\text{---}(COR^2O)_z\text{---}COR^1 \quad (I)$$

in which $R^1CO$ is an acyl group containing 1 to 22 carbon atoms or a hydroxyfatty acyl group containing 16 to 22 carbon atoms, $(OR^2CO)$ is the residue of a hydroxyfatty acyl group containing 16 to 22 carbon atoms, x is a number of 5 to 150 and y and z are numbers of 2 to 75, the group $(OC_2H_4)_x$ making up 10 to 20% by weight of the molecular weight, for stabilizing water-in-oil emulsions.

DETAILED DESCRIPTION OF THE INVENTION

The block copolyesters corresponding to formula I are particularly suitable as emulsifiers for water or aqueous phases in polar oil components. Polar oil components are understood to be oils which contain 1 to 4 ester groups or ether oxygen atoms in the molecule. Accordingly, one preferred embodiment of the invention is characterized in that monofunctional or polyfunctional esters of $C_{8-22}$ fatty acids or $C_{8-22}$ fatty alcohols or ethers of $C_{8-22}$ fatty alcohols containing 16 to 70 carbon atoms are used as oil components for the water-in-oil emulsion.

The polar oil components are preferably liquid at 20° C.

Examples of such oil components, which are preferred for the production of water-in-oil emulsions, are fatty acid esters such as, for example, butyl stearate, cetyl oleate, isotridecyl stearate, oleyl oleate, jojoba oil, ethylene glycol diisostearate; fatty alcohol esters such as, for example, oleyl acetate, isotridecyl benzoate and diisooctyl sebacate; and triglyceride oils such as, for example, olive oil, sunflower oil, soya oil or palm oil.

The production of the block copolyesters is known per se from the literature and may be carried out, for example, by initially preparing the lipophilic part of the molecular by polycondensation of a hydroxyfatty acid. Either y or z moles of a hydroxyfatty acid may be condensed onto a non-hydroxylated carboxylic acid with the formula $R^1COOH$ as starter molecule. Alternatively, the hydroxyfatty acid $HO\text{---}R^2\text{---}COOH$ may simply be subjected to polycondensation, in which case the hydroxyfatty acid itself serves as starter molecule (i.e. 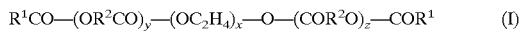).

Suitable hydroxyfatty acids are, for example, 12-hydroxystearic acid and other synthetic hydroxyfatty acids obtainable, for example, by hydro-genation of the epoxyfatty acids containing 16 to 22 carbon atoms. Particularly preferred hydroxyfatty acids are ricinoleic acid and hydrogenated castor oil fatty acid. The polycondensation is preferably carried out in the presence of an acidic catalyst (for example methane sulfonic acid) with elimination of water using toluene or xylene as entraining agent until the removal of water and the reduction in the acid value indicate an average degree of condensation (y or z) of 2 to 75 and preferably 5 to 30.

Accordingly, block copolyesters of formula I in which the groups $(OR^2CO)_y$ and $(COR^2O)_z$ are residues of ricinoleic acid or hydrogenated castor oil fatty acid with a degree of condensation y or z of 5 to 30 are preferably used. The hydrophilic part of the molecule with the formula $(OC_2H_4)_x$ consists of a polyethylene glycol having an average degree of polymerization x of 5 to 150 and preferably 10 to 70. Polyethylene glycols such as these are commercially available.

The block copolyesters may be produced by condensation of the lipophilic hydroxyfatty acid polycondensate with the polyethylene glycol, 2 moles of water being eliminated per mole of polyethylene glycol. However, the condensation of the hydroxyfatty acid may also be carried out with the hydroxyfatty acid itself and with the polyethylene glycol in a single stage in one and the same reaction mixture. 1 Mole of water should be eliminated per mole of hydroxyfatty acid and an acid value of less than 5 (mg KOH/g) should be achieved in the block copolyester.

Accordingly, the easiest way of producing block copolyesters suitable for the purposes of the invention is to condense 10 to 20% by weight of a polyethylene glycol with 80 to 90% by weight of a ricinoleic acid or hydrogenated castor oil fatty acid with elimination of 1 mole of water per mole of hydroxyfatty acid. The HLB value of these block copolyesters as calculated in accordance with the following formula:

$$HLB = \frac{100 - L}{5}$$

(where L is the percentage content of lipophilic acyl groups ($R^1CO$ and $R^2CO$) in % by weight) is therefore between about 2 and 4.

The present invention also relates to a process for the production of water-in-oil emulsions in which block copolyesters corresponding to general formula I are added as emulsifiers to the oil phase in a quantity of 0.1 to 10% by weight (based on the weight of the oil phase). The emulsification of the resulting emulsion concentrates with water or with an aqueous phase may be carried out by standard mechanical emulsification processes.

To this end, the aqueous phase is mixed with the oil phase using shear energy (stirring, shaking, ultrasonication, slit homogenization, rotor/stator homogenizers).

Using the block copolyesters of formula I suitable for the purposes of the invention, up to 80% by weight of water or aqueous solutions can be emulsified into an oil phase. Accordingly, the present invention also relates to water-in-oil emulsions containing 1 to 80% by weight of inner aqueous phase and 20 to 99% by weight of oil phase, the oil phase containing 0.1 to 10% by weight of a stabilizer and a block copolyester corresponding to general formula I being present as stabilizer.

The water-in-oil emulsions according to the invention are suitable for various industrial and cosmetic applications. Emulsions of the water-in-oil type based on polar oil components, for example natural triglyceride oils and natural and synthetic fatty acid and fatty alcohol esters, are of considerable importance above all in the field of cosmetic and pharmaceutical emulsions. Accordingly, the subject of the present invention is of particular value for these particular applications.

The following Examples are intended to illustrate the invention.

EXAMPLES

Emulsion concentrates were prepared by dissolving 0.1% by weight, 0.2% by weight and 0.5% by weight of the following block copolyesters in various oil components by dissolving the block copolyesters in oil at 60° C.

| | |
|---|---|
| Block copolyester A: | 16.7% by weight of polyethylene glycol MW:1000 |
| | 83.3% by weight of ricinoleic acid |
| Block copolyester B: | 16.7% by weight of polyethylene glycol MW:600 |
| | 83.3% by weight of ricinoleic acid |
| Block copolyester C: | 16.7% by weight of polyethylene glycol MW:1550 |
| | 83.3% by weight of ricinoleic acid |
| Block copolyester D: | 16.7% by weight of polyethylene glycol MW:3000 |
| | 83.3% by weight of ricinoleic acid |
| Block copolyester E: | 22.0% by weight of polyethylene glycol MW:1000 |
| | 78.0% by weight of ricinoleic acid |
| Block copolyester F: | 11.8% by weight of polyethylene glycol MW:1000 |
| | 88.2% by weight of ricinoleic acid |

Emulsions were then prepared from

25% by weight of the emulsion concentrates and 75% by weight of water by mixing the emulsion concentrates and the water, heating the resulting mixture to 60° C. and then homogenizing it for 3 minutes in a Heidolph test-tube shaker.

Stable w/o emulsions were obtained with the emulsion concentrates of 0.1 to 0.5% by weight of block copolyesters A to D in 99.5 to 39.9% by weight of sunflower oil 0.1 to 0.5% by weight of block copolyesters A to D in 99.5 to 39.9% by weight of di-n-octyl ether 0.1 to 0.5% by weight of block copolyesters A to D in white oil (Winog 40)

0.1 to 0.5% by weight of block copolyesters E and F in di-n-octyl ether 0.1 to 0.5% by weight of block copolyesters E and F in sunflower oil.

We claim:

1. A method comprising stabilizing a water-in-oil emulsion with an effective amount of a block copolyester of the formula I:

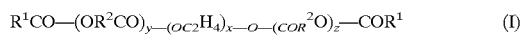

$$R^1CO-(OR^2CO)_y-(OC_2H_4)_x-O-(COR^2O)_z-COR^1 \quad (I)$$

wherein $R^1CO$ is an acyl group having 1 to 22 carbon atoms or a hydroxyfatty acyl group having 16 to 22 carbon atoms, $(OR^2CO)$ is the residue of a hydroxyfatty acyl group having 16 to 22 carbon atoms, x is a number of 5 to 150, y is a number of 2 to 75, z is a number of 2 to 75, and $(OC_2H_4)_x$ makes up 10% to less than 20% of the molecular weight of said block copolyester.

2. A method according to claim 1, wherein the oil phase of said emulsion comprises a monofunctional or polyfunctional ester of $C_{8-22}$ fatty acids or $C_{8-22}$ fatty alcohols or ethers of $C_{8-22}$ fatty alcohols having 16 to 70 carbon atoms.

3. A method according to claim 2, wherein $(OR^2CO)_y$ and $(COR_2O)_z$ are residues of ricinoleic acid or of hydrogenated castor oil fatty acid with an average degree of condensation y and z of 5 to 30.

4. A method according to claim 2, wherein x is 10 to 70.

5. A method according to claim 1, wherein $(OR^2CO)_y$ and $(COR_2O)_z$ are residues of ricinoleic acid or of hydrogenated castor oil fatty acid with an average degree of condensation y and z of 5 to 30.

6. A method according to claim 5, wherein x is 10 to 70.

7. A method according to claim 1, wherein x is 10 to 70.

8. A process for the production of water-in-oil emulsions comprising adding to the oil phase of said emulsions 0.1% to 10% by weight, based on the weight of the oil phase, of a block copolyester of the formula I:

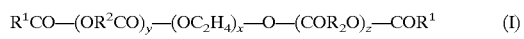

$$R^1CO-(OR^2CO)_y-(OC_2H_4)_x-O-(COR_2O)_z-COR^1 \quad (I)$$

wherein $R^1CO$ is an acyl group having 1 to 22 carbon atoms or a hydroxyfatty acyl group having 16 to 22 carbon atoms, $(OR^2CO)$ is the residue of a hydroxyfatty acyl group having 16 to 22 carbon atoms, x is a number of 5 to 150, and y is a number of 2 to 75, z is a number of 2 to 75, and $(OC_2H_4)_x$ makes up 10% to less than 20% of the molecular weight of said block copolyester.

9. A water-in-oil emulsion comprising by weight, 1% to 80% inner aqueous phase and 20% to 99% oil phase, said oil phase comprising 0.1 to 10% by weight, based on the weight of the oil phase, of a block copolyester of the formula I:

$$R^1CO-(OR^2CO)_y-(OC_2H_4)_x-O-(COR^2O)_z-COR^1 \quad (I)$$

wherein $R^1CO$ is an acyl group having 1 to 22 carbon atoms or a hydroxyfatty acyl group having 16 to 22 carbon atoms, $(OR^2CO)$ is the residue of a hydroxyfatty acyl group having 16 to 22 carbon atoms, x is a number of 5 to 150, y is a number of 2 to 75, z is a number of 2 to 75, and $(OC_2H_4)_x$ makes 10% to less than and 20% of the molecular weight of said block copolyester.

* * * * *